(12) United States Patent  (10) Patent No.: US 7,648,524 B2
Zhang et al. (45) Date of Patent: Jan. 19, 2010

(54) POROUS TENDON ANCHOR

(75) Inventors: Renwen Zhang, Wayne, NJ (US);
Daniel Lawrynowicz, Cornwall, NY
(US); Nicholas Nai Guang Dong, Little
Falls, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 438 days.

(21) Appl. No.: 11/318,172

(22) Filed: Dec. 23, 2005

(65) Prior Publication Data

US 2007/0162022 A1 Jul. 12, 2007

(51) Int. Cl.
*A61B 17/84* (2006.01)
(52) U.S. Cl. ........................................ 606/323; 606/331
(58) Field of Classification Search ............. 606/72, 606/73, 300, 301, 304, 313, 314, 326, 327, 606/329, 323, 324, 331; 623/13.14, 13.11–13.13, 623/13.15, 13.18, 20.17, 20.21
See application file for complete search history.

(56) References Cited

U.S. PATENT DOCUMENTS

| | | | |
|---|---|---|---|
| 2,180,866 A * | 11/1939 | Cryer | 403/369 |
| 3,805,300 A * | 4/1974 | Tascon-Alonso et al. | 623/13.14 |
| 3,973,277 A | 8/1976 | Semple et al. | |
| 4,369,003 A * | 1/1983 | Brandstetter | 405/259.3 |
| 4,467,478 A | 8/1984 | Jurgutis | |
| 4,597,766 A | 7/1986 | Hilal et al. | |
| 4,605,414 A | 8/1986 | Czajka | |
| 4,668,233 A | 5/1987 | Seedhom et al. | |
| 4,708,132 A | 11/1987 | Silvestrini | |
| 4,744,793 A | 5/1988 | Parr et al. | |
| 4,755,183 A | 7/1988 | Kenna | |
| 4,772,286 A | 9/1988 | Goble et al. | |
| 4,834,752 A | 5/1989 | Van Campen | |
| 4,870,957 A | 10/1989 | Goble et al. | |
| 4,927,421 A | 5/1990 | Goble et al. | |
| 4,997,433 A | 3/1991 | Goble et al. | |
| 5,013,520 A | 5/1991 | Hummel | |
| 5,062,843 A | 11/1991 | Mahony, III | |
| 5,129,902 A | 7/1992 | Goble et al. | |
| 5,147,362 A | 9/1992 | Goble et al. | |

(Continued)

FOREIGN PATENT DOCUMENTS

FR 2582517 12/1986

(Continued)

*Primary Examiner*—Eduardo C Robert
*Assistant Examiner*—Ellen Rust
(74) *Attorney, Agent, or Firm*—Lerner, David, Littenberg, Krumholz & Mentlik, LLP

(57) ABSTRACT

An anchor for fixing a ligament or tendon replacement in a bore formed in a bone has two parts. A first partially cylindrical part has a semi-circular bore therethrough extending along an axis. The bore tapers conically inwardly with respect to the axis from a larger radius at a first end to a smaller radius at second end. The outer surface of the partially cylindrical part is spaced at a constant radius from the axis between the first and second ends. The first and second parts have side walls formed between the bore and the outer surface which walls extend along a plane which forms an angle with respect to the central axis. When the two parts are engaged along their side wails and slide with respect to the axis the outer diameter of the two parts enlarges.

35 Claims, 4 Drawing Sheets

U.S. PATENT DOCUMENTS

| | | | |
|---|---|---|---|
| 5,233,730 A * | 8/1993 | Milne et al. ................ | 24/136 R |
| 5,263,802 A | 11/1993 | Fichot et al. | |
| 5,324,308 A | 6/1994 | Pierce | |
| 5,383,878 A | 1/1995 | Roger et al. | |
| 5,417,518 A | 5/1995 | Bierwith | |
| 5,454,811 A | 10/1995 | Huebner | |
| 5,529,424 A | 6/1996 | Neubert et al. | |
| 5,630,301 A * | 5/1997 | Sieg ........................ | 52/223.13 |
| 5,632,748 A | 5/1997 | Beck, Jr. et al. | |
| 5,707,395 A * | 1/1998 | Li ............................... | 606/232 |
| 5,720,753 A | 2/1998 | Sander et al. | |
| 5,964,769 A | 10/1999 | Wagner et al. | |
| 6,190,411 B1 | 2/2001 | Lo | |
| 6,360,636 B1 | 3/2002 | Elftmann | |
| 6,379,361 B1 | 4/2002 | Beck, Jr. et al. | |
| 6,517,579 B1 | 2/2003 | Paulos et al. | |
| 6,554,862 B2 * | 4/2003 | Hays et al. ................ | 623/13.14 |
| 6,562,044 B1 | 5/2003 | Cooper | |
| 6,562,071 B2 * | 5/2003 | Jarvinen ................... | 623/13.14 |
| 6,736,847 B2 | 5/2004 | Seyr et al. | |
| 6,883,280 B2 * | 4/2005 | Hayes ...................... | 52/223.13 |
| 7,360,342 B2 * | 4/2008 | Hayes et al. ............. | 52/223.14 |
| 2003/0009220 A1 | 1/2003 | Seyr et al. | |
| 2003/0153981 A1* | 8/2003 | Wang et al. ............... | 623/22.21 |
| 2004/0191106 A1 | 9/2004 | O'Neill et al. | |
| 2005/0284049 A1* | 12/2005 | Hayes et al. ............. | 52/223.13 |
| 2006/0117683 A1* | 6/2006 | Hayes et al. ............. | 52/223.13 |
| 2006/0147332 A1 | 7/2006 | Jones et al. | |

FOREIGN PATENT DOCUMENTS

| | | |
|---|---|---|
| FR | 2582518 | 12/1986 |
| WO | WO-8403036 | 8/1984 |

* cited by examiner

POROUS TENDON ANCHOR

BACKGROUND OF THE INVENTION

The present invention relates to a tendon anchor to be used within the knee or other parts of the body.

The present invention is directed to the reconstruction of the anterior cruciate ligament (ACL) and the posterior cruciate ligament (PCL). The ACL helps stabilize the knee joint, and prevents posterior displacement of the femur on the tibia in hyperextension of the knee joint.

The ACL is sometimes torn during sports or as a result of traumatic stresses. Ligament reconstruction with allograft or autograft tissue has been shown to improve joint function and provide long term improvement in restoration of physical activity. A typical surgical procedure for ligament replacement and reconstruction involves obtaining a tissue graft or a suitable synthetic graft to replace the damaged ligament. A graft may come from either another part of the patient's body (autograft), from a cadaver donor (allograft), or the graft may be synthetically manufactured.

Structurally, the ACL attaches to a depression in the front of the intercondylar eminence of the tibia and extends posterior-superiorly to the medial wall of the lateral femoral condyle. Partial or complete tears of the ACL are common, comprising over a 120,000 cases annually in the United States.

The preferred treatment of the torn ACL is ligament reconstruction, using a bone-ligament-autograft. Methods for placement of such bone-ligament-bone grafts are generally described in Goble et al., U.S. Pat. Nos. 4,772,286; 4,870,957; 4,927,421; 4,997,433; 5,129,902; and 5,147,362. Other methods are shown in U.S. Pat. No. 4,400,833 to Kurland; U.S. Pat. No. 4,467,478 to Jurgustis; U.S. Pat. No. 4,597,766 to Hillal et al.; U.S. Pat. No. 4,668,233 to Seedhom et al.; U.S. Pat. No. 4,744,793 to Parr et al.; U.S. Pat. No. 4,834,752 to Vankampen; and U.S. Pat. No. 5,013,520 to Rosenberg.

Although the use of a bone-tendon-bone graft may provide the advantage of effective healing due to the efficient integration of the bone graft to the bone host, the harvesting of a bone-tendon-bone graft typically results in extensive morbidity to the donor knee joint. It is, therefore, often preferable to harvest grafts made up entirely of tendon tissue such as the hamstring. However, it has been found to be more difficult to effectuate and maintain accurate fixation of such grafts throughout the healing period where high-tension forces of the knee may act to disrupt the graft construct.

ACL reconstruction procedures generally include the formation of a tunnel through the patient's femur and tibia bones and implanting a natural ligament or tendon or a synthetic ligament in the bone tunnel which eventually attaches itself to the bone and holds the tibia and femur together.

In order to anchor the ligament within the bore or tunnel a device is necessary for grasping the ligament which can then integrate itself with the bone surrounding the bore. In the past, devices such as interference screws have been used when a bone-tendon-bone system has been used. See Mahony, U.S. Pat. No. 5,062,843; or Roger et al., U.S. Pat. No. 5,383,878; Steininger et al., U.S. Pat. No. 5,425,767; and Hubner U.S. Pat. No. 5,454,811. Interference screws function by creating a tight fit between the bone graft and the surrounding bone. Such a system may result in the tendon being damaged which can result in impeded healing or loosening of the interference fixation.

There has been a need for a ligament anchor which can fix the ligament in the bone bore which anchor includes a porous inner and outer surface for tissue ingrowth.

SUMMARY OF THE INVENTION

One aspect of the present invention is to provide a tendon anchor which can be used to anchor a tendon or ligament within a bone bore in the femur and tibia.

It is another aspect of the invention to provide a tendon anchor which can expand externally under load to securely anchor the tendon within the bone tunnel or within a tunnel from within an implant.

It is yet another aspect of the invention to provide a tendon anchor having an inner and outer surface which is porous and preferably being made from porous material such as titanium foam.

When the entire tendon anchor is made from the titanium foam, it has been shown to host new bone ingrowth and ongrowth when implanted in bone with new tendon-like tissues growing in the pores of the inside of the tendon anchor. Thus the titanium foam anchor acts as an interface between the bone and tendon. The tendon anchor can be made in the form of a tube and a tendon graft can be passed through the tube and can be fixed to the end of the tube by passing the Bunnell criss-cross stitch through the poles on the tube, which is then tightly fit into the bone tunnel. The suture can also be fixed outside the bone tunnel in any manner. To avoid the possible difficulty in passing the tendon graft through the tube, the tube can be fabricated in two halves.

Preferably, the device consists of two half tubes split along a small angle wedge creating a first and a second part. In the preferred embodiment the first and second parts are not identical but form a tube of constant diameter when longitudinally aligned. The internal diameter of the tube consists of a tapered cone with multiple barbs locking against the direction towards the larger diameter. After the bony anchoring site is drilled to create a bore, the larger end of one half tube is inserted into the bone, the tendon with suture attached at the end is inserted and the suture is passed through the exit hole in the bore. The smaller end of the second half of the tube is then inserted with force which will lead to the expansion of the two half tubes due to the wedge split. The tendon is pulled against the inner taper of the tubular body which will further expand the foam tube for tight contact to the tendon and the bone. The tubular body can have internal barbs to help prevent the tendon from slipping out. The final lock is achieved by fixing the suture anchor to an anchor outside the bone tunnel.

Thus attachment of tendon to bone can be used in primary ACL reconstruction surgery, semitendinosus-gracillis (hamstring) and quadricept tendon autografts. Use of these ligaments is associated with less graft harvesting morbidity than the patella tendon graft. However, fixation of tendon to bone tunnel remains a concern using these tendons.

Use of allografts and synthetic tendon substitutes have been tried with the success of using this material in tendon reconstruction depending on the healing of the material with bone. The fixation must be secure to prevent changes of the position and tension of the graft. In addition, fixation is a prerequisite for early rehabilitation. The tendon anchor of the present invention can be used as an interface in these procedures.

These and other aspects of the present invention are achieved by a tendon anchor for fixing a tendon in a bore in a bone which anchor has an elongated tubular body extending along the longitudinal axis. The body comprises first and second parts each of the parts having an elongated outer surface and an elongated inner bore. The inner bore and the outer surface defines a wall therebetween having elongated side surfaces. The side surfaces taper in a radial direction with respect to the axis from a first end toward the second end of the tubular body.

A plane containing the side surfaces of each of the first and second parts crosses the longitudinal axis of the tubular body preferably midway between the first and second ends of the body, and preferable at a small angle of about 1.5-5°. The tendon anchor outer surface may have a bone engaging element such as a circumferential ridge extending outwardly therefrom. The inner bore of each of the first and second parts includes plurality of inwardly extending tendon engaging elements which may be in the form of inwardly extending barbs having sharpened points.

In the preferred embodiment, the inner and outer surface of each of the first and second parts has a tissue ingrowth surface thereon. The inner and outer surface may have different porosities, the outer for bone ingrowth and the inner for tendon tissue ingrowth. Preferably, the entire tubular body is made of a porous metal structure such as titanium foam. The average pore size of the titanium foam is preferably 100 to 1000 micron more preferably 300 to 400 microns. The biocompatible porous metal may be titanium, titanium alloy, tantalum, ceramic or alternatively a porous biodegradable material such as PGA or PLLA may be used.

BRIEF DESCRIPTION OF THE DRAWINGS

FIGS. 4, 4a are end views looking in at the left side of FIGS. 2 and 2a;

FIGS. 5, 5a are end views looking at the right hand end of FIGS. 2 and 2a; and

DETAILED DESCRIPTION

Figure 1:
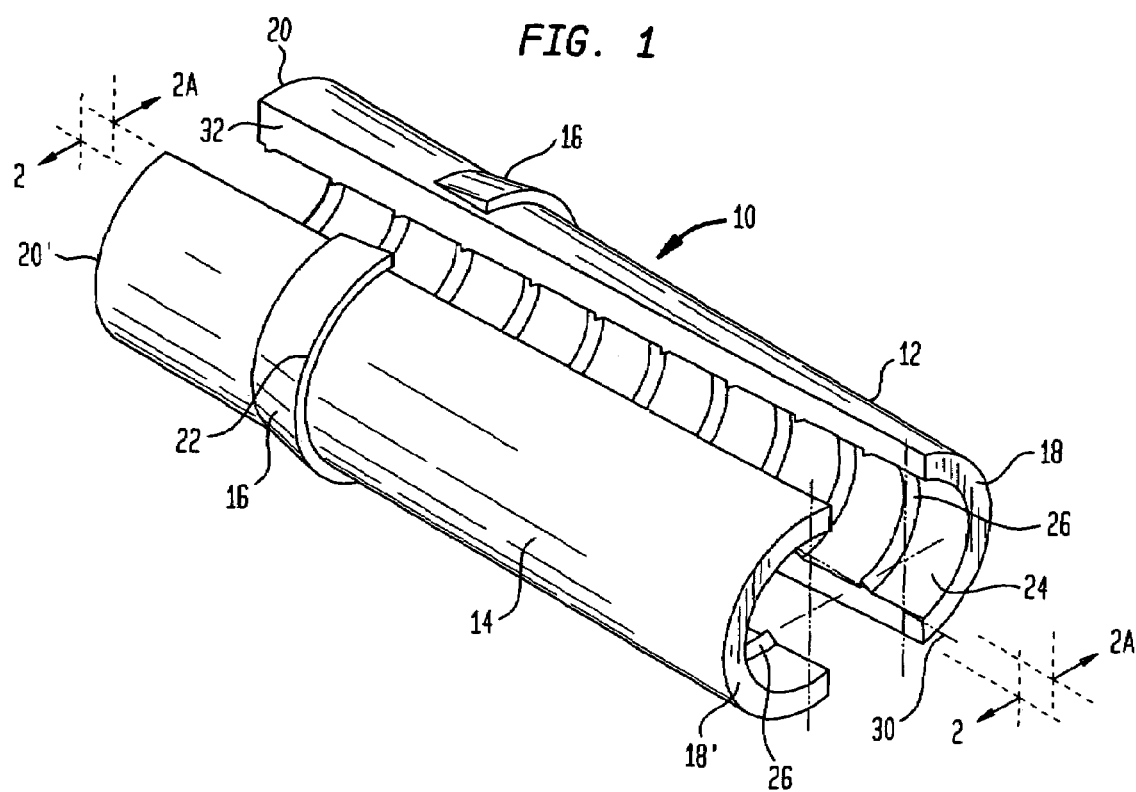
FIG. 1 is an exploded isometric view of the two-part porous tendon anchor of the present invention.
Figure 1A:
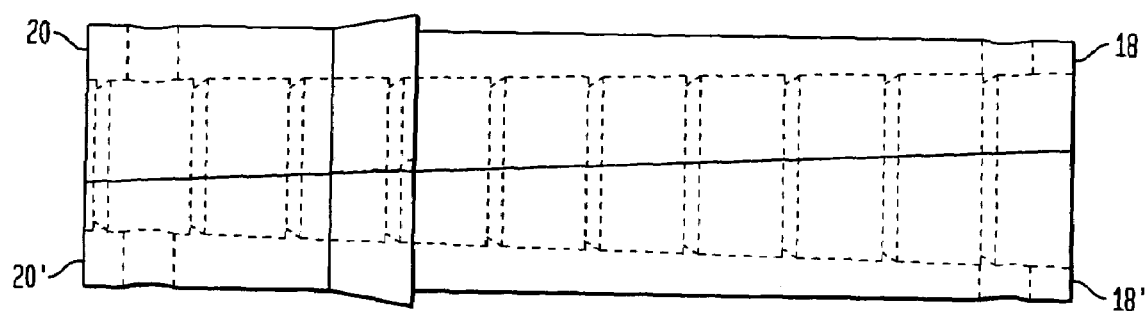
FIG. 1a is a side elevation view of the assembled tendon anchor of FIG. 1.

Referring to FIGS. 1 and 1a there are shown isometric views and side views of the two-piece tendon anchor generally denoted at 10. Tendon anchor 10 consists of a first part 12 and a second part 14 which are generally wedge-shaped such that movement of part 12 with respect to part 14 increases the overall diameter of the anchor 10. Each part 12 and 14 includes an outer circumferential ridge 16 located intermediate a first end 18 and 18' of the first and second part 12 and 14 respectively and a second end 20 and 20' of 12 and 14 respectively. Ridge 16 has a relatively sharp edge 22 designed to imbed itself in the bone as the anchor 10 expands by the relative movement of part 12 with respect to part 14. In first part 12 end 20 is the thicker wedge wall and in second part 14 end 20' is the thicker wedge wall. Ends 18 and 18' are the thinner wedge wall since the inner diameter of the anchor is larger at this end. The circumference of parts 12 and 14 is tapered. End 18' is the larger circumferentially extending end of wedge of part 14 and end 18 is the smaller circumferentially extending end of wedge 12. End 20' is the smaller circumferentially extending end of wedge part 14 and end 20 is the larger end of part 12.

Each part 12, 14 has a hollow interior 24 designed to receive a replacement tendon or ligament (not shown). The replacement ligament may be an autograft or allograft tendon or ligament, such as a patella Achilles tendon or may be a synthetic tendon such as those made from collagen or polymers. The internal surface 24 of both parts 12 and 14 includes a series of ridges 26 which function to imbed themselves into the replacement ligament or tendon.

Figure 2:
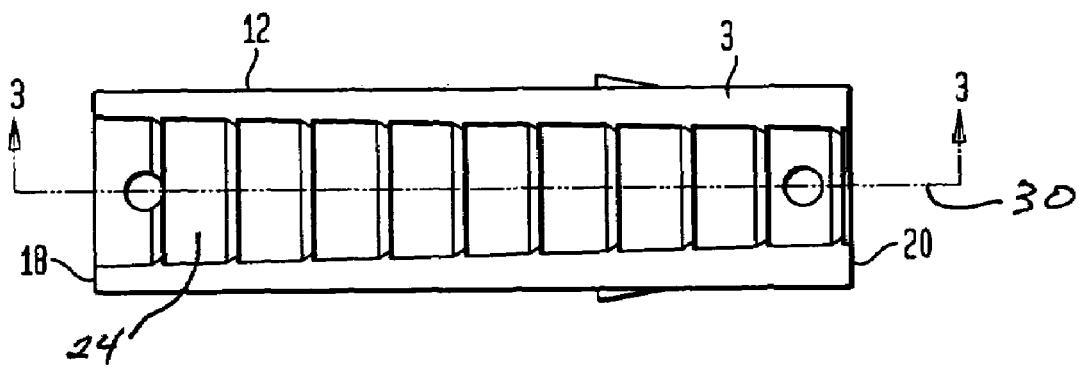
FIGS. 2, 2a are respective side elevation views of each of the parts of the two-part porous tendon anchor shown in FIG. 1.
Figure 2A:
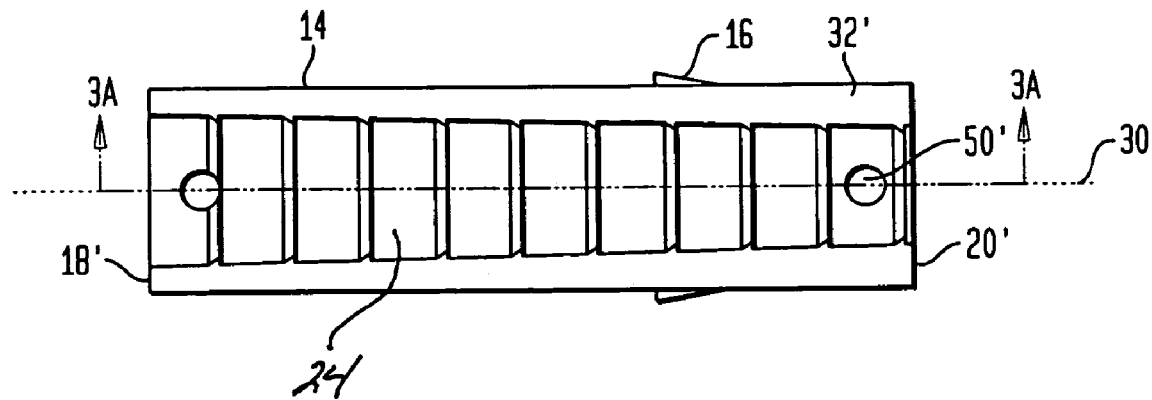

Referring to FIGS. 2 and 2a there is shown respective side elevation views of one of the parts 12 and 14. As can be seen in FIGS. 2, 2a inner surface 24 of each part 12, 14 tapers inwardly from ends 18, 18' to ends 20, 20'. In the preferred embodiment the inner bore taper is between 1.5° and 5° with ridges 26 spaced at intervals along the entire length of parts 12 and 14. In the preferred embodiment the surfaces 24 of each part 12 or 14 are part circular centered about an axis 30 through the center of each part 12 and 14.

Figure 3:
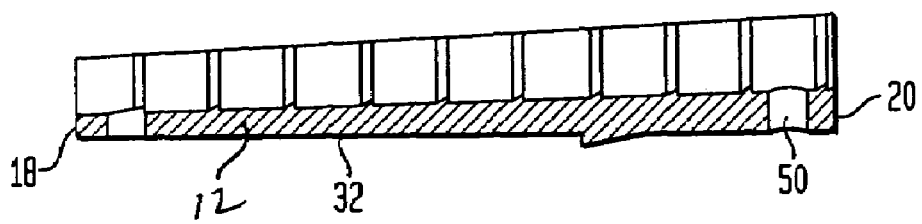
FIG. 3, 3a are cross-sectional views of the tendon anchor parts shown in FIGS. 2, 2a along lines 3-3 and 3a-3a respectively.
Figure 3A:
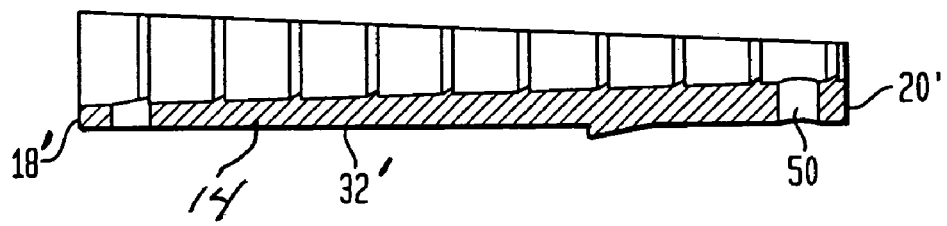

Referring to FIG. 3, 3a there are shown respective cross-sections of the tendon anchor parts of FIG. 2, 2a showing a cross-section wall 32 which increases in thickness from end 18, 18' to end 20, 20'. In addition wall 32 of part 12 tapers in circumferential extent from a large circumference at end 20, to a smaller circumference at end 18. In part 14 the circumferential taper increases from a smaller circumference at end 20' to a larger circumference at end 18'. In the preferred embodiment the larger circumferential extent is greater than 180°. Wall 32' increases in thickness on moving from end 18' to end 20'. In the preferred embodiment the taper of wall 32, 32' is constant between the first and second ends with the increase in radius at end 20 of part 12 equal to the reduction in radius at end 18. The same reduction in radius occurs from end 18' to end 20' of part 14. Thus a plane containing surfaces 32, 32' of each of the first and second parts 12 and 14 crosses axis 30 at a point between end 18, 18' and end 20, 20'. In the preferred embodiment the angle formed by the plane containing surfaces 32, 32' and axis 30 is between 1° and 10° and more preferably between 3° to 6°.

As best seen in FIGS. 2, 2a ridge 16 tapers outwardly on moving from the side thereof adjacent end 20, 20' towards a side thereof facing end 18, 18' at an angle α. In the preferred embodiment α is 10°.

Figure 4:
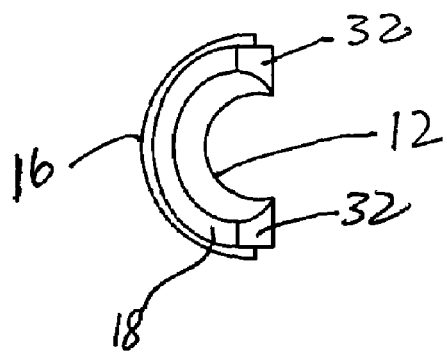
Figure 5:
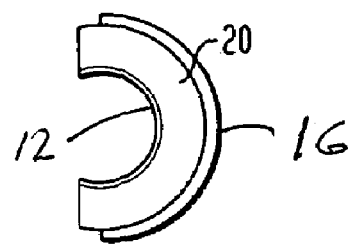
Figure 4A:
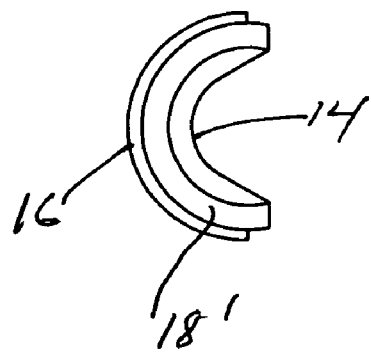
Figure 5A:
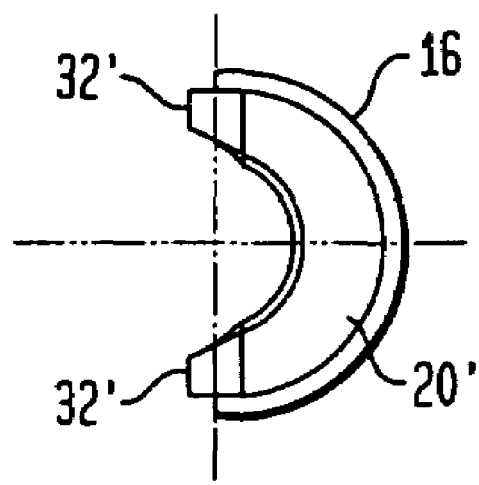

Referring to FIGS. 4, 4a and 5, 5a there is respectively shown end views of the tendon anchor parts of FIG. 2, 2a of ends 18, 18' and 20, 20' respectively. Each end view shows ridge 16 with FIG. 4, 4a showing the thinner end wall of end 18, 18' and FIGS. 5, 5a showing the thicker end wall of end 20, 20'. FIGS. 4a and 5 show end 18' or end 20 with walls 32, 32' tapering from a larger circumferential extent across the longitudinal axis 30 toward the end with the smallest circumferential extent while FIGS. 4 and 5a show walls 32, 32' increasing in circumferential extent from a smaller circumferential extent at end 18, 20' across the axis 30 to the end with the larger circumferential extent.

Figure 6:
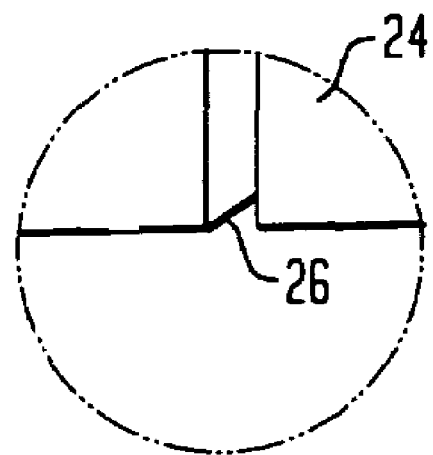
FIG. 6 is an enlarged view of detail A of FIG. 2 showing the circumferential ridge for engaging the replacement ligament or tendon.

Referring to FIG. 6 there is shown an enlarged view of detail A of FIG. 2, 2a in which a single ridge 26 is shown extending into the part's circular bore of each piece 12 and 14. When surfaces 32, 32' of each piece 12 and 14 are placed adjacent one another surface 24 of each piece forms a circular bore conically tapering outwardly on moving from end 18 to end 20 of part 12 and outwardly from end 18' to 20' of part 14. While when ends 18, 18' and 20, 20' of each piece are aligned along axis 30 the tendon anchor 10 has a constant outer diameter. As parts 12 and 14 are slid along surface 32, 32' in opposite directions along axis 30 with respect to one another, the diameter increases because of the taper of surfaces 32, 32' with respect to axis 30. This causes a wedging action which locks the tendon anchor in a bone bore as will be described below.

To use the tendon anchor of the present invention the surgeon first drills the typical bore in a bone forming the joint, such as the tibia and femur, for receiving the replacement tendon or ligament. In the case of ACL reconstruction, a bone tunnel in the tibia and in the femur is prepared for receiving the replacement ligament. The larger circumferential end 20 of the first part 12 of the tendon anchor for the femur is inserted into the bone bore of the femur. The graft, preferably with a suture attached at its end, is advanced through the bone tunnel and out through the anterolateral femoral cortex. The smaller circumferential end 20' of the second tendon anchor part 14 is then inserted and force is applied to the larger end, which causes the expansion of the two parts due to the wedge-shaped split formed by surfaces 32, 32'. While the second part is pushed tension is kept on the graft to prevent folding of the graft inside the tendon anchor. The internal ridges 26 help prevent the tendon from slipping out after the whole anchor is embedded in the bone tunnel. The tendon is fixed to the femur at the lateral cortex.

Likewise the tendon anchor first part 12 for the tibial fixation is introduced first into the knee. The larger circumferential part 20 of the anchor is inserted into the bone tunnel towards the portal at the tibial cortex. The second part 14 is then inserted with end 20, first to embrace the tendon graft. With the graft in tension, the second part is pushed along the bone tunnel. A hook can be inserted through the tibial tunnel to pull the anchor until it is totally in the bone tunnel. The suture is fixed on the cortex of the tibia. The internal ridges 26 help prevent the tendon from slipping out. The final locking of the tendon is achieved by fixing the suture to an anchor outside the bone tunnel.

In the preferred embodiment the entire bone anchor 10 first and second parts 12, 14 are formed from a porous titanium or titanium alloy. Preferably the porous titanium is manufactured by selective laser sintering (SLS). To make the porous tendon ligament anchor using SLS, a layer of metal powder is deposited on a substrate. The substrate is not intended to be an integral part of the finished product. After an individual layer of powder is deposited, a scanning process may be preformed to selectively melt the powder to form portions of a plurality of predetermined unit cells. The scanning process includes scanning a laser beam onto the metal powder.

As successive layers are deposited and scanned a structure is built from one end to an opposite end. The structure includes a plurality of predetermined unit cells. The unit cells provide the structure with interconnecting pores as well as porosity. The size of the pores and porosity as well as other factors may all be predetermined.

In one preferred embodiment the size of the pores of the porosity of the porous tendon/ligament anchor are specifically chosen to provide the structure for bone and ligament ingrowth.

The method of producing a three-dimensional porous tissue in-growth structure preferably includes depositing a first layer of a powder made from a metal selected from the group consisting of titanium, titanium alloys, stainless steel, cobalt chrome alloys, tantalum and niobium onto a substrate. The layer of powder is then scanned using a laser beam. The laser beam has a power, and scans the powder layer for a period of time with a point distance. The power of the laser beam is preferably within the range of 5 to 1000 watts. The exposure time is in a range between 100 μsec to 1000 μsec. The laser beam scans the powder layer to form a portion of a plurality of predetermined unit cells. The predetermined unit cells include struts having cross-sectional dimensions. The cross-section of the struts may be any regular of irregular shape. A few such examples include circular, rectangular, cubic cross-sections or the like. The laser power is preferably 90.5 W, the exposure time is 1000 μsec and the point distance is 90 μm.

The manufacturing method also preferably includes depositing at least one additional layer of the powder onto the first layer and repeating the step of scanning the additional layers with a laser beam for at least one of the deposited layers in order to continue forming the predetermined unit cells which eventually form the tendon anchor.

The predetermined unit cells may take the shape of the first and second tendon anchor parts. The unit cells may be in the shape of a tetrahedron, dodecahedron or octahedron as well as other symmetrical structures. As mentioned, the unit cells may not have such uniformity and may have an irregular shape. The unit cells may also be truncated, which includes eliminating some of the struts, which form a unit cell. Truncated unit cells located at the exterior surface of a built product provide a barbed effect to the product.

A porosity range is programmed for at least one deposited powder layer and scanning the layer in a manner to provide the deposited layer with porosity within the predetermined porosity range. Portions of the powder layers may be fused and or sintered to the base or core. The base or core is then separated from the finished first or second part of the tendon anchor.

Generally, the method of producing a three-dimensional construct such as the first and second tendon anchor parts includes loading a file of the parts component into an engineering design package. The component is scaled down in the file from its original size. A Boolean operation is next performed to subtract the scaled down component from the original component. This creates a jacket. The jacket can then be processed using a bespoke application that populates the jacket with a repeating open cellular structure.

The open cellular structure is then sliced using the bespoke application to a predetermined thickness. Such a system by fabricating parts using laser sintering is taught in U.S. Ser. Nos. 10/704,270 (US2004/0191106) and 11/027,421, the disclosure of which is incorporated herein by reference.

The main body of the file component jacket is loaded into a user interface program and the jacket is sliced into layers having a predetermined thickness. Hatching is then applied to the file component jacket as required to build a construct and the jacket is merged with the open cellular lattice structure. Once a representation has been obtained the depositing and scanning steps of the SLS process may be conducted to build the tendon anchor parts.

While laser sintering is the preferred method of fabricating the porous tendon anchor, injection molding could also be used wherein the titanium powder is mixed with a polymeric binder and then injection molded into the desired shape. The polymeric binder is then removed by a solvent and the part sintered to form the high strength tendon anchor implant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An anchor for fixing a tendon or a ligament in a bone comprising:

an elongated tubular body having a bore extending along a longitudinal axis, said tubular body comprising first and second independent parts slidably contacting each other, the first and second independent parts each having an outer circumferential surface along a length thereof parallel to the longitudinal axis, and each having an elongated partial inner bore, said partial inner bore and said outer circumferential surface defining a wall therebetween having two elongated planar side surfaces, said bore tapering in a radial direction with respect to said longitudinal axis from a first end towards a second end of said tubular body, a first end of the first and second independent parts having a wall thickness that is less than a second end, the outer circumferential surface tapering on the first and second parts in opposite directions so that the first end of the first part with a smaller wall thickness is closer to the first end of the second part with a larger outer circumferential surface, the sliding contact between the first and second parts occurring on said facing planar side surfaces of the first and second parts during movement therebetween in the direction of the longitudinal axis such that the tubular body is capable of mounting a tendon or ligament within the bore.

2. The tendon anchor as set forth in claim 1 wherein a plane containing the side surfaces of each of said first and second part crosses said longitudinal axis of said tubular body.

3. The tendon or ligament anchor as set forth in claim 2 wherein the plane crosses said longitudinal axis at an angle of 1.5° range.

4. The tendon or ligament anchor as set forth in claim 2 wherein the thickness of said walls of said first and second parts along said plane increases on moving from said first end to said second end.

5. The tendon or ligament anchor as set forth in claim 1 wherein each of said first and second parts has at least one bone engaging element extending outwardly therefrom.

6. The tendon or ligament anchor as set forth in claim 5 wherein the at least one bone engaging element is a circumferential ridge.

7. The tendon or ligament anchor as set forth in claim 1 wherein the inner bore of each of said first and second parts includes at least one of inwardly extending tendon engaging elements.

8. The tendon or ligament anchor as set forth in claim 7 wherein the tendon engaging element are inwardly extending circumferential ridges.

9. The tendon or ligament anchor as set forth in claim 1 wherein a tissue contacting surface of each of said first and second parts has a tissue ingrowth surface thereon.

10. The tendon or ligament anchor as set forth in claim 9 wherein the tissue ingrowth surface is formed from a biocompatible foam.

11. The tendon or ligament anchor as set forth in claim 1 wherein the tubular body is made of a biocompatible foam.

12. The tendon or ligament anchor as set forth in claim 1 wherein with respect to said longitudinal axis, the circumferential extent of said first and second parts tapers from larger to smaller from end to end.

13. The tendon or ligament anchor as set forth in claim 12 wherein the taper is between 1 and 10°.

14. The tendon or ligament anchor as set forth in claim 1 wherein a plane continuing said side surfaces of said first and second part forming said tubular body intersects said longitudinal axis of said tubular body at a point intermediate said first and second ends thereof.

15. The tendon or ligament anchor as set forth in claim 14 wherein said intersection point is midway between said first and second ends.

16. The tendon or ligament anchor as set forth in claim 15 wherein said plane crosses said longitudinal axis forming an angle of between 1.5 and 5° therebetween.

17. The tendon or ligament anchor as set forth in claim 14 wherein said intersection point is midway between said first and second ends.

18. The tendon or ligament anchor as set forth in claim 15 wherein said plane crosses said longitudinal axis forming an angle of between 1.5 and 5° therebetween.

19. The tendon or ligament anchor as set forth in claim 1 wherein the body is made of a porous biodegradable material.

20. The tendon or ligament anchor as set forth in claim 1 wherein with respect to said longitudinal axis the inner bore of said first and second parts tapers inwardly from said first end towards said second end at an angle of 1.5°.

21. The tendon or ligament anchor as set forth in claim 1 wherein a plane continuing said side surfaces of said first and second part forming said tubular body intersects said longitudinal axis of said tubular body at a point intermediate said first and second ends thereof.

22. The tendon or ligament anchor as set forth in claim 1 wherein the body is made of a porous biodegradable material.

23. An anchor for fixing a ligament or a tendon replacement in a bore formed in a bone comprising:

first and second independent partially cylindrical parts each having a partial bore therethrough extending along an axis and an outer circumferential surface extending parallel to the axis, said bore tapering with respect to said axis from a larger radius at a first end to a smaller radius at a second end, the outer circumferential surface of said partially cylindrical part spaced at a constant radius from said bore axis between said first and second ends, each of said first and second parts having a wall formed between said bore and said outer circumferential surface, said wall extending at an angle with respect to said axis, said wall defining two planar side surfaces, a first end of the first and second parts having a wall thickness that is less than a second end, the outer circumferential surface of the first and second parts tapering in opposite directions so that the first end of the first part with a smaller wall thickness is closer to the first end of the second part having a larger outer circumferential surface, the side surfaces of the first part slidably contacting the side surfaces of the second part on movement between the first and second parts with respect to the axis such that the first and second parts are capable of mounting a tendon or ligament therein.

24. The tendon anchor as set forth in claim 23 wherein a plane containing the side surfaces of each of said first and second part crosses said longitudinal axis of said tubular body.

25. The tendon or ligament anchor as set forth in claim 24 wherein the plane crosses said longitudinal axis at an angle of 1.5° range.

26. The tendon or ligament anchor as set forth in claim 24 wherein the thickness of said walls of said first and second parts along said plane increases on moving from said first end to said second end.

27. The tendon or ligament anchor as set forth in claim 23 wherein each of said first and second parts has at least one bone engaging element extending outwardly therefrom.

28. The tendon or ligament anchor as set forth in claim 27 wherein the at least one bone engaging element is a circumferential ridge.

29. The tendon or ligament anchor as set forth in claim 23 wherein the inner bore of each of said first and second parts includes at least one of inwardly extending tendon engaging elements.

30. The tendon or ligament anchor as set forth in claim 29 wherein the tendon engaging element are inwardly extending circumferential ridges.

31. The tendon or ligament anchor as set forth in claim 23 wherein a tissue contacting surface of each of said first and second parts has a tissue ingrowth surface thereon.

32. The tendon or ligament anchor as set forth in claim 31 wherein the tissue ingrowth surface is formed from a biocompatible foam.

33. The tendon or ligament anchor as set forth in claim 23 wherein the tubular body is made of a biocompatible foam.

34. The tendon or ligament anchor as set forth in claim 33 wherein the average pore size of the titanium foam is from 100 microns to 1000 microns.

35. The tendon anchor as set forth in claim 34 wherein the pore size is from 300 to 400 microns.

* * * * *